United States Patent [19]

Latch et al.

[11] Patent Number: 6,111,170

[45] Date of Patent: Aug. 29, 2000

[54] TALL FESCUE ENDOPHYTES

[75] Inventors: Garrick Cecil Morland Latch, Palmerston North; Michael John Christensen, Ashurst; Brian Anthony Tapper, Palmerston North; Herrick Sydney Easton, Palmerston North; David Edward Hume, Palmerston North; Lester Ronald Fletcher, Christchurch, all of New Zealand

[73] Assignee: New Zealand Pastoral Agriculture Research Institute Limited, Hamilton, New Zealand

[21] Appl. No.: 09/085,442

[22] Filed: May 27, 1998

[30] Foreign Application Priority Data

May 27, 1997 [NZ] New Zealand ............................ 314925

[51] Int. Cl.$^7$ ............................... A01H 5/00; A01H 5/10; A01H 15/00
[52] U.S. Cl. ....................... 800/320; 800/298; 435/254.1; 424/93.5
[58] Field of Search ..................................... 800/298, 320, 800/265; 435/254.1; 424/93.5

[56] References Cited

U.S. PATENT DOCUMENTS 4,940,834  7/1990  Hurley ..................................... 800/200

FOREIGN PATENT DOCUMENTS

| 639084 | 10/1991 | Australia .......................... C12N 1/14 |
| 0 753 259 A2 | 1/1997 | European Pat. Off. ....... A01N 63/04 |
| 233083 | 3/1991 | New Zealand . |
| 96/39807 | 12/1996 | WIPO .............................. A01H 5/12 |

OTHER PUBLICATIONS

Ball, O.J–P et al. "Effect of Selected Isolates of Acremonium Endophytes on Adult Black Beetle (*Heteronychus arator*) Feeding" (1994) Proc. 47$^{th}$ N.Z. Plant Protection Conf. 227:231.

Barker, D.J. et al. "Effect of water deficit on alkaloid concentrations in perennial ryegrass endophyte associations" (1993) Hume D.E., Latch G.C.M. and Easton H.S. (Eds) Proc. of the Second International Symposium on Acremonium/Grass Interactions, pp. 67–71 AgResearch, Palmerston North, New Zealand.

Christensen, M.J. et al. Variation among isolates of Acremonium endophytes (*A. Coenophialum* and possibly *A. Typhinium*) from tall fescue (*Festuca arundinacea*) (1991) *Mycol. Res.* 95:1123–1126.

Christensen, M.J. et al. "Taxonomy of Acremonium endophytes of tall fescue (*Festuca arundinacea*), meadow fescue (*F. Pratensis*) and perennial rye–grass (*Lolium perenne*)" (1993) *Mycol. Res.* 97(9): 1083–1092.

Christensen, M.J. "Variation in the ability of Acremonium endophytes of perennial rye–grass (*Lolium perenne*), tall fescue (*Festuca arundinacea*) and meadow fescue (*F. Pratensis*) to form compatible association in the three grasses" (1995) *Mycol Res.* 99:446–470.

Christensen, M.J. "A concise guide to the taxonomy of Acremonium Endophytes, in particular those from *Lolium perenne* and *Festuca Arundinacea*" (1993) Proceedings of the Second International Symposium on Acremonium/grass Interactions, pp. 59–61.

Dymock, J.J. et al. "Effects of Endophyte produced Mycotoxins on Argentine Stem Weevil and the Cutworm *Graphania Mutans*" (1989) Proceedings of the 5$^{th}$ Australasian Conference on Grassland Invertebrate Ecology, Stahl, (Ed.) DD Printing, Victoria pp. 35–43.

Dymock, J.J. et al. "Novel combinations of endophytes in ryegrasses and fescues and their effects on Argentine Stem Weevil (*Listronotus bonariensis*) feeding" (1989) Proceedings of the 5$^{th}$ Australian Conference on Grassland Invertebrate Ecology, P.P. Stahle, (ed). pp. 28–34.

Easton, H.S., "Will Endophyte Strain Affect Variety Performance?" (1993) Proceedings of the Second International Symposium on Acremonium/Grass Interactions. Eds. Hume, Latch & Easton: pp. 195–199.

Gallagher, R.T. et al. "Tremorgenic Neurotoxins from Perennial Ryegrass Causing Ryegrass Staggers Disorder of Livestock: Structure Elucidation of Lolitrem B" (1984) *J. Chem. Soc. Chem. Commun.* 614–616.

Gaynor, D.L. et al. "Insect Resistance, Animal Toxicity and Endophyte–Infected Grass" (1986), Proceedings of the New Zealand Grassland Association, 47:115–120.

Koga, H. et al. "Incompatibility of some grass/Acremonium endophyte associations" (1993) *Mycol. Res.* 97(10):1237–1244.

Latch, G.C.M. et al. "Artificial infection of grasses with endophytes" (1985) *Ann.Appl.Biol.* 107:17–24.

Latch, G.C.M., "Plant Improvement using Endophytic Fungi " (1989) Proceedings XVI International Grassland Congress pp. 345–346.

Latch, G.C.M. et al. "Five Endophytes of Lolium and Festuca in New Zealand" (1984) *Mycotaxon* Vol. XX, No. 2, 535–550.

Latch, G.C.M. et al. "Aphid detection of endophyte infection in tall fescue" (1985) *New Zealand Journal of Agricultural Research* 28:129–132.

(List continued on next page.)

*Primary Examiner*—Lynette R. F. Smith
*Assistant Examiner*—Melissa L. Kimball
*Attorney, Agent, or Firm*—Greenlee Winner and Sullivan PC

[57] ABSTRACT

Selected endophytes of the genus Neotyphodium (formerly Acremonium) form stable synthetic combinations with tall fescue hosts (*Festuca arundinacea*). The combinations have improved resistance to invertebrate pests as compared to tall fescue cultivars not containing such endophytes. The particular combinations of the invention have reduced toxicity to livestock as compared to naturally occurring endophyte/tall fescue combinations. The seven preferred endophytes are AR501, AR502, AR510, AR542, AR572, AR577 and AR584.

9 Claims, No Drawings

OTHER PUBLICATIONS

Morgan–Jones, G. et al. "Notes on Hyphomycetes LI. An endophyte of *Festuca arundinacea* and the anamorph of *Epichloe typhina*, a new taxa in one of two new sections of *Acremonium*" (1982) *Mycotaxon 15*:311–318.

Rolston, M.P. et al. "Viability of Lolium endophyte fungus in seed stored at different moisture contents and temperatures" (1986) *New Zealand Journal of Experimental Agriculture* 14:297–300.

Rowan, D.D. et al. "An efficient method for the isolation of peramine, an insect feeding deterrent produced by the fungus *Acremonium lolii*" (1989) *Journal of Natural Products* 52(1):193–195.

Rowan, D.D. et al. "Peramine, a novel insect feeding deterrent from ryegrass infected with the endophyte *Acremonium loliae*" (1986) *J. Chem. Soc., Chem. Commun.* 935–936.

Siegel, M.R. et al. "Acremonium Fungal Endophytes of Tall Fescue and Perennial Ryegrass: Significance and Control" (1985) *Plant Disease* 69(2):179–183.

Siegel, M.R. et al. "Fungal Endophytes of Grasses" (1987) *Ann.Rev.Phytopathol.* 25:293–315.

Tapper, B.A. et al. "Detection and Measurement of the Alkaloid Peramine in Endophyte–infected Grasses" (1989) *Journal of Chomatography* 464:133–138.

West, C.P. et al. "Role of Acremonium in drought, pest, and disease tolerances of grasses" (1993) Proceedings of the Second International Symposium on Acremonium/Grass Interactions. Plenary Papers. (Eds) Hume, Latch & Easton: 195–199.

Williams, J.G.K. et al. "DNA polymorphisms amplified by arbitrary primers are useful as genetic markers" (1990) *Nucleic Acids Research* 18(22):6531–6535.

Yates, S.G. et al. "Detection of Ergopeptine Alkaloids in Endophyte Infected, Toxic Ky–31 Tall Fescue by Mass Spectrometry/Mass Spectrometry" (1985) *J. Agric. Food Chem.* 33:719–722.

Yoder, O.C. "*Cochliobolus heterostrophus*, Cause of Southern Corn Leaf Blight" (1988) *Advances In Plant Pathology* 6:93–112.

Fraser, M.L. et al. "The Role of Endophytes in Integrated Pest Management for Turf"; *Handbook of Integrated Pest Management for Turfgrass & Ornamentals,* (1994) CRC Press, Inc. pp. 521–528.

Funk, C.R. et al. "Role of Endophytes in Grasses Used for Turf and Soil Conservation"; *Biotechnology of Endophytic Fungi of Grasses,* Charles W. Bacon & James F. White, Jr. Eds. (1994) CRC Press, Inc. pp. 201–209.

Johnson, M.C. et al. "Infection of Tall Fescue with *Acremonium coenophialum* by Means of Callus Culture"; (1986) *Plant Disease* 70(5):380–382.

O'Sullivan, B.D. et al. "Infection of Plantlets, Derived from Ryegrass and Tall Fescue Meristems, with Acremonium Endophytes"; Proc. of the $2^{nd}$ Symposium on Acremonium Grass Interactions, D.E. Hume, G.C.M. Latch & H.S. Easton, Eds., 1993, Palmerston North, New Zealand.

Barker et al. Proceedings of the Second International Symposium on Acremonium/Grass Interactions. pp. 59–61, 1993.

Christensen. Proceedings of the Second Internation Symposium on Acremonium/Grass Interactions. pp. 67–71, 1993.

De Battista et al. Agronomy Journal. 82:651–654, 1990.

TALL FESCUE ENDOPHYTES

CROSS REFERENCE TO RELATED APPLICATIONS

This application claims priority from New Zealand Patent Application No. 314925 filed May 27, 1997.

STATEMENT RE FEDERALLY SPONSORED RESEARCH AND DEVELOPMENT

Not applicable.

BACKGROUND OF THE INVENTION

It is known from New Zealand patent specification 233,083 that synthetic combinations of endophyte/herbage cultivars can be made which are resistant to pests and can be less toxic to grazing animals than naturally occurring combinations. The desired properties were achieved by selecting synthetic combinations which produced relatively high levels of peramine and relatively low levels of or no lolitrem B in ryegrass.

It has been found that the ergopeptine alkaloid, ergovaline, was produced in a synthetic endophyte/perennial tall fescue combination and that livestock grazing on the combination had an adverse physiological reaction to ergovaline under specific conditions.

Naturally occurring endophytes in populations of tall fescue cultivars in the United States of America (for example, Kentucky 31 tall fescue) generally have high levels of toxicity in the warm seasons. We have screened many such combinations but have been unable to locate any which produce levels of ergovaline sufficiently low to be candidate selections for making acceptable synthetic endophyte/tall fescue combinations. We have been able to find a few strains from Mediterranean locations which are able to meet the primary selection criteria of effective absence of ergovaline and a satisfactory level of peramine, an insect resistance factor.

It is an object of this invention to go some way towards avoiding the above mentioned disadvantages and achieving the aforementioned desiderata or at least to offer the public a useful choice.

SUMMARY OF THE INVENTION

This invention relates to selected endophytes in the genus Neotyphodium (formerly Acremonium) which form stable synthetic combinations with tall fescue hosts (cultivars and selected breeding lines of *Festuca arundinacea*) and which combinations have improved resistance to invertebrate pests in comparison to the same grasses lacking endophyte and which have reduced toxicity to livestock as compared to naturally occurring endophyte/tall fescue combinations.

For the purposes of this specification the expression "synthetic endophyte/tall fescue combination" means the combination of an endophyte and a culturally improved tall fescue variety each of which has been isolated from nature, but the combination of which does not exist in nature.

Accordingly, in a first aspect, the invention may be said broadly to consist in an axenic culture of an endophyte which in synthetic combination with a tall fescue cultivar produces levels of peramine in excess of 5 ppm in aggregates of herbage cut above about 1 cm above soil level and levels of ergovaline of less than 0.1 ppm in herbage cut at or above about 1 cm above soil level and less than 0.5 ppm ergovaline in crowns below about 1 cm above soil level, excluding roots.

In another embodiment the invention may be said broadly to consist in a synthetic combination of an endophyte as defined immediately above with a tall fescue cultivar.

In another embodiment, the invention may be said broadly to consist of an axenic culture of an endophyte selected from the group consisting of AR501, AR502, AR510, AR542, AR572, AR577 and AR584, AGAL deposit nos. NM98/04681, NM98/04677, NM98/04678, NM98/04675, NM98/04679, NM98/04680 and NM98/04676, respectively, dated May 12, 1998.

In another embodiment the invention may be said broadly to consist in a synthetic combination of tall fescue and an endophyte selected from AR501, AR502, AR510, AR542, AR572, AR577 and AR584.

Preferably the tall fescue cultivar is a temperate European type tall fescue cultivar.

Preferably said tall fescue cultivar is selected from the group consisting of Grasslands Roa, Grasslands Advance, Kentucky 31, Georgia 5, Jesup, Jackal and Quantum.

Preferably said synthetic combination is made by inoculating a said tall fescue cultivar with a said axenic culture of a said endophyte.

In another alternative said synthetic combination is made by crossing a said synthetic endophyte/tall fescue combination with an endophyte free tall fescue cultivar to form a new tall fescue cultivar infected with said endophyte.

The invention may also be said broadly to consist in seeds of said synthetic combination. Preferably said seeds are harvested from tall fescue plants inoculated with said endophyte. Alternatively, said seeds are harvested from plants of said synthetic endophytes/tall fescue combination grown from seeds harvested from tall fescue plants inoculated with said endophyte.

DETAILED DESCRIPTION OF THE INVENTION

The invention consists in the foregoing and also envisages constructions of which the following gives examples.

EXAMPLE 1

Selected Endophytes

The seven preferred Neotyphodium endophyte strains according to this invention belong to two taxonomic groups. The first group consists of strains AR501, AR502, AR510, AR572 and AR577. They form colonies on potato dextrose agar (PDA) which are slow grow ing (radial growth <0.15 mm/day at 20° C.), raised, brain-like, white, cottony with the underside brown in colour. Conidia (5–8 $\mu$m in length) are sparsely produced in colonies of AR501, AR502, AR572 and AR577, but readily produced in colonies of AR510.

The second group comprises strains AR542 and AR584 which conform to the species description for *Neotyphodium coenophialum* (=*Acremonium coenophialum*) (Morgan-Jones and Gams, 1982). Colonies on PDA are white, cottony, hyphae sometimes aggregated into ropes, radial growth rate is 0.2–0.25 mm/day at 20° C. and the underside of the colony is pale brown. Conidia are readily produced in culture and are 8–14 $\mu$m in length.

(a) Endophytes AR501 and AR502

These endophytes are strains of a Neotyphodium spp. from a collection of seed from Southern Spain. The endophytes are held in a culture collection at the Grasslands site in Palmerston North of the New Zealand Pastoral Agriculture Research Institute Limited (AgResearch). The cultures are also deposited at the Australian Government Analytical Laboratories (AGAL) in Sydney, Australia under deposit nos. NM98/04681 and NM98/04677 dated May 12, 1998.

-FAM), 4,7,2',7'-tetrachloro-6-carboxyfluorescein (TET) and 4,7,2',4',5',7'-hexachloro-6-carboxyfluorescein (HEX). The primer sequence pairs are given in Table 1.

TABLE 1

Primer Sequence Pairs for Defining Microsatellite Loci of Endophytes in planta

| Locus | Primers | Primer Sequences | 5'-Dye |
|---|---|---|---|
| B4 | B4.1 (SEQ ID NO:1) | 5'-TGG ACT CGA CTT GCC CTC TCT CAG | 6-FAM |
|  | B4.2 (SEQ ID NO:2) | 5'-TGC GAG CAG CGT TTG CGT GTG CGT |  |
| B6 | B6.1 (SEQ ID NO:3) | 5'-GGC ATG GTA TGG GCA ATG AGT GTC | 6-FAM |
|  | B6.2 (SEQ ID NO:4) | 5'-CTG CTG CGA TGT TTT GTA CTG TGG |  |
| B9 | B9.1 (SEQ ID NO:5) | 5'-AAT CGT TGT GCG AGC CAT TCT GGC | TET |
|  | B9.4 (SEQ ID NO:6) | 5'-GCC CCG TCA TGC ATT ATC TCC TTG |  |
| B10 | B10.1 (SEQ ID NO:7) | 5'-CGC TCA GGG CTA CAT ACA CCA TGG | TET |
|  | B10.2 (SEQ ID NO:8) | 5'-CTC ATC GAG TAA CGC AGG CGA CG |  |
| B11 | B11.1 (SEQ ID NO:9) | 5'-CAT GGA TGG ACA AGA GAT TGC ACG | HEX |
|  | B11.4 (SEQ ID NO:10) | 5'-TTC ACT GCT ACA ATT CTG TGG AGC |  |

(b) AR510

This strain was isolated from a seed collection from Algeria and is a Neotyphodium spp. A specimen of this strain is held at Palmerston North and in the AGAL under deposit no. NM98/04678 dated May 12, 1998.

(c) AR542 and AR584

These two strains were isolated from tall fescue originating from Morocco and are of the species *Neotyphodium coenophialum*. Specimens of these strains are held at Palmerston North and in the AGAL under deposit nos. NM98/04675 and NM98/04676 dated May 12, 1998.

(d) AR572 and AR577

These strains have been isolated from seed collections from Southern Spain and Southern Portugal respectively. They are of Neotyphodium spp. which rarely produce spores under standard cultural conditions. These strains are held at Palmerston North and in the AGAL under deposit nos. NM98/04679 and NM98/04680 dated May 12, 1998.

EXAMPLE 2

Identification of Endophytes by Polymorphic DNA Microsatellite Analysis

The endophytes AR501, AR502, AR510, AR572 and AR577 are representatives of one group, and AR542 and AR584 are representatives of another group. They are distinguished from all other known groups of Neotyphodium endophytes occurring naturally in cultivars of tall fescue by the characterisation of alleles at one or more polymorphic genetic loci. The distinguishing characteristics are the number of distinct and the size of microsatellite sequences amplified by the polymerase chain reaction (PCR) technique using selected amplification primers.

Five sets of PCR primer pairs, one of each pair labelled with a fluorescent dye phosphoramidite at the 5'-end for detection purposes, have been selected to define the microsatellite loci for characterisations of endophyte in planta. The fluorescent dye labels are 6-carboxyfluorescein (6

To characterise each endophyte a sample of genomic DNA is prepared from 100 mg to 200 mg fresh weight of pseudo-stems of endophyte-infected grass plants by the FastDNA Kit method for plant tissue (Bio 101, Inc., Vista Calif., USA). The DNA is used for PCR amplification with the primer pairs either individually or combinations of primers pairs for loci B4 with B6, B9 with B10 and B11 alone.

The polymerase chain reactions are prepared in 1 2.5 $\mu$l volumes containing mM Tris-HCl, 1.5 mM $MgCl_2$, 50 mM KCl, pH 8.3 in the presence of 50 $\mu$M of each deoxynucleotide triphosphate, 200 nM of each primer, 0.08 U $\mu l^{-1}$ Taq DNA polymerase (Boehringer Mannheim GmbH), and approximately 400 pg $\mu l^{-1}$ total genomic DNA. The PCR is conducted for 30 cycles with temperature steps of 1 min at 94°, 2 min at 65°, and 1 min at 72° followed by a final extension of 10 min at 72° with a PC-960 or FTS-960 thermocycler (Corbett Research, Mortlake, Australia).

No PCR amplification product is observed when genomic DNA from plants lacking endophyte is used in PCR with the selected primer pairs.

Appropriate portions from the PCR amplifications for each endophyte sample, mixed together with GS-500 TAMRA as an internal size standard, are analysed by polyacrylamide gel electrophoresis (4.25%) on the ABI Prism 377 DNA Sequencer (Perkin-Elmer Corp., Foster City, Calif., USA). The size of the products is measured using GeneScan Analysis 2.1 software (Perkin-Elmer Corp.).

The use of a fluorescent dye on just one primer of each primer pair gives the size measurement of only one of the strands of the amplified DNA sequences of each allele. This simplifies the interpretation of results. The use of different dyes for loci where amplification products might occur in overlapping size ranges means that a single combination of PCR products can be analysed for each endophyte.

The results for individual endophyte PCR microsatellite loci size analysis are considered in conjunction with information from other endophytes and interpreted bearing in mind that the PCR reaction using Taq polymerase tends to add a single additional adenine to amplification products. This gives a proportion of product one base higher in length than the actual sequence being amplified. The length of the PCR product, considered for the purposes of comparing endophytes, is the best estimate of the size actually amplified and may be one base less than the size reported by the GeneScan Analysis system. On occasions both the actual size and a size one unit greater may be resolved by the instrument and reported. For the purposes of comparing estimated sizes a tolerance of ±0.5 of a size unit may be accepted as being within a single size range after allowance has been made for the possibility of the PCR product being recorded as of one additional length unit in size.

The endophytes AR501, AR502, AR510, AR572 or AR577 can be distinguished from other endophytes by their particular pattern of microsatellites. The endophytes AR542 and AR584 can also be distinguished from other endophytes by their particular pattern of microsatellites, which is different from the pattern seen with the typical *Neotyphodium coenophialum* endophytes of tall fescue which accumulate both ergovaline and peramine. These three distinct typical patterns are detailed in Table 2.

TABLE 2

Summary of Microsatellite Data for Distinguishing the Endophytes

| Locus | Allele size(s) AR501, AR502, AR510 AR572 & AR577 | Allele size(s) AR542 & AR584 | Allele size(s) Common *N. coenophialum* |
|---|---|---|---|
| B4 | 119.9 | 102.4 and/or 103.7 | 100.0 & 102.4 |
| B6 | 172.6 | 192.7 | 193.7 |
| B9 | absent | 271.9 | 271.9 |
| B10 | 172.1 & 180.8 | 163.4 & 172.1 | 163.5, 172.1 & 180.8 |
| B11 | 128.6 | 182.0 & 192.7 | 149.8 & 192.7 |

Some variation, notably for the B4 locus, may apply with a single allele apparently absent or undetected or of a different size but with sufficient commonality of pattern to characterise the endophyte as part of its respective group. Two groups of endophytes infecting tall fescue, typically accumulating peramine but not ergovaline, can thus be distinguished by polymorphic DNA microsatellite analysis as different from any other grouping or classification of known *N. coenophialum* endophytes.

EXAMPLE 3

Extraction of Endophytes from their Natural Host (a) From plants

Leaf sheath tissue of tall fescue plants containing natural endophytes was removed from the plant and surface sterilized by dipping it into 70% ethanol for 5 seconds before placing it in a 10% solution of sodium hypochlorite (0.5% available chlorine) and shaking for 5 minutes. The tissue was then rinsed in sterile water and cut into 2–3 mm pieces.

(b) From seed

Seeds containing endophyte were surface sterilized by soaking for 20 minutes in 50% sulphuric acid followed by rinsing several times in sterile water, soaking in 10% sodium hypochlorite solution for 20 minutes and rinsing again in sterile water.

All surface sterilized tissues were placed on potato dextrose agar containing antibiotics (100 μg/ml streptomycin+ 100 μg/ml penicillin) in Petri dishes and incubated at 20° C. for 4–5 weeks. By this time colonies of endophytes had sufficient growth to enable them to be used for inoculating grass seedlings.

EXAMPLE 4

Inoculation of Seedlings a) Growing of Seedlings for Inoculation

Inoculation of seedlings is done in a sterile environment so it is necessary to surface sterilize the seeds before they are germinated. The seeds are soaked for 20 minutes in a 50% solution of sulphuric acid in water, washed in sterile water, soaked for 20 minutes in a 20% solution of a chlorine based bleach sold under the trade mark "Janola" and then washed in sterile water. The seeds are then dried on sterile filter paper in a laminar flow cabinet. These dried seeds are placed 10/plate on the surface of 4% water agar in Petri plates and incubated in the dark at 20° C. for 5–7 days. The plates are examined daily for contaminant fungi not killed by surface sterilization and contaminated seedlings are removed with a scalpel.

(a) Inoculation of Seedlings

Colonies of endophyte are grown on Potato Dextrose Agar in Petri plates at 20° C. Seedlings which are 5–7 days old are inoculated with endophyte mycelium by making a longitudinal slit with a scalpel in the meristematic region of the seedling stem. Mycelium is introduced into the slit with a needle or scalpel. The Petri plates are sealed with tape and incubated in the dark at 20° C. for 2–4 days. The plates are then removed and placed on a bench in the light or in an illuminated incubator for 3–4 days prior to planting the seedlings in compost-filled root-trainers.

EXAMPLE 5

Growing of Seedlings, Harvesting of Seeds

Infected seedlings, after testing for verification of infection with the candidate endophyte and for compliance with the criteria noted in Table 1, were naturally vernalised through the winter and placed in isolation with other tall fescue plants of the same cultivar (so that pollen from tall fescue not of the same cultivar was excluded). When seed was set, the originally infected isolated plants were harvested individually. A sample of seed from each infected isolated plant was tested to verify the presence and identity of endophyte within the seed. A sample of seed from each infected isolated plant was sown to verify that progeny plants conformed to the description of the original inoculated cultivar. Plants originally infected with the same endophyte strain, and for which seed passed the above two tests, were defined as the "infected parent plants" for that strain. The seed from the different infected parent plants was bulked (the same weight from each infected parent plant) to form a seed lot which was subsequently multiplied under normal seed certification procedures, with the frequency of endophyte infection of each harvest verified by seed squash.

EXAMPLE 6

Measurement of Alkaloids

The levels of alkaloids for each of the various defined synthetic endophyte/tall fescue combinations determined by the methods of Barker et a. (1993) are set out in Table 3.

TABLE 3

Alkaloid Levels

|  | Ergovaline | Peramine |
|---|---|---|
| Herbage[1] | <0.1 ppm | >5 ppm |
| Crown[2] | <0.5 ppm | |

[1]Herbage aggregates above 1 cm from soil level.
[2]Cut below about 1 cm from soil level and excluding roots.

EXAMPLE 7

Agronomic Trials

Preliminary results from trials in Georgia, USA, with tall fescue cultivars Georgia 5 and Jesup infected with a selection of endophytes averaged a 53% increase in yield in comparison with endophyte-free controls as set out in Table 4. Row length was 1.2 m and the trial was carried out during 1996–97 at Eatonton. These data also show the synthetic endophyte/tall fescue combinations were not significantly different from the wild type in yield but always out-yielded endophyte-free controls.

TABLE 4

Dry Matter Yield (gm per row)

| Endophyte | Georgia 5 | Jesup |
|---|---|---|
| Wildtype | 576 | 439 |
| Endophyte free | 364 | 340 |
| AR501 | 483 | 499 |
| AR502 | — | 424 |
| AR510 | — | 637 |
| AR542 | 573 | 616 |

EXAMPLE 8

Grazing Trial

Separate pastures were sown at an AgResearch campus near Lincoln, New Zealand with Kentucky 31 tall fescue containing wild type endophyte, Kentucky 31 which was endophyte-free, and Kentucky 31 which was infected with AR501. The pastures were grazed with Coopworth sheep (first grazing with adult ewes, and the second with 5 month old lambs). The various animal responses are set out below in Table 5.

Serum prolactin is very sensitive to low levels of ergovaline. It was used in the trials as an indicator of intoxication with ergopeptine alkaloids in the grazing animals.

For all animal responses in each of the two grazing periods the AR501 and endophyte-free treatments were significantly different from the wild type endophyte treatment. In all cases there was no difference between AR501 and endophyte-free treatments.

TABLE 5

Summary of animal performance on Kentucky 31 tall fescue: without endophyte, with its natural endophyte or with AR501

Liveweight change

| Liveweight change (gm/head/day) | 1st grazing | 2nd grazing |
|---|---|---|
| Kentucky 31 wild-type | 86 | −36 |
| Kentucky 31 endophyte-free | 245 | 79 |
| Kentucky 31 AR501 | 254 | 86 |

Respiration rate
1st grazing

| Respiration/30 sec | 4/10/96 | 10/12/96 | 23/12/96 |
|---|---|---|---|
| Kentucky 31 wild-type | 80 | 112 | 106 |
| Kentucky 31 endophyte-type | 60 | 81 | 70 |
| Kentucky 31 AR501 | 64 | 84 | 72 |

2nd grazing

| Respiration/30 sec | 13/2/97 | 26/2/97 |
|---|---|---|
| Kentucky 31 wild-type | 80 | 116 |
| Kentucky 31 endophyte-free | 63 | 88 |
| Kentucky 31 AR501 | 62 | 91 |

Body Temperature
1st grazing

| Body Temperature °C. | 4/10/96 | 10/12/96 | 23/12/96 |
|---|---|---|---|
| Kentucky 31 wildtype | 39.7 | 40.3 | 40.1 |
| Kentucky 31 endophyte-free | 39.3 | 39.7 | 39.3 |
| Kentucky 31 AR501 | 39.4 | 39.8 | 39.5 |

2nd grazing

| Body temperature °C. | 23/2/97 | 25/2/97 |
|---|---|---|
| Kentucky 31 wild-type | 40.4 | 40.9 |
| Kentucky 31 endophyte-free | 39.9 | 40.4 |
| Kentucky 31 AR501 | 40.0 | 40.6 |

Serum Prolactin
1st grazing

| Prolactin ng/ml | 4/12/96 | 10/12/96 |
|---|---|---|
| Kentucky 31 wild-type | 10 | 22 |
| Kentucky 31 endophyte-free | 138 | 327 |
| Kentucky 31 AR501 | 132 | 277 |

Further grazings of the trial set up in 1996 were carried out in 1997/98 and a summary of the results from this trial is presented in Table 6.

TABLE 6

Summary of Animal Performance in 1997/98 on Kentucky 31 Tall Fescue, without Endophyte, with its Natural Endophyte or with AR501

|  | Live weight gain gm/day | Temperature °C. | Respiration Breaths/30 sec |
|---|---|---|---|
| Spring | | | |
| Kentucky 31 Wild-type | 91 | 40.3 | 110 |
| Kentucky 31 Endophyte-free | 115 | 39.9 | 94 |
| Kentucky 31 AR501 | 130 | 40.0 | 92 |
| Summer | | | |
| Kentucky 31 Wild-type | −77 | 40.5 | 103 |
| Kentucky 31 Endophyte-free | 29 | 39.9 | 63 |
| Kentucky 31 AR501 | 32 | 39.9 | 59 |

The data from the second year of the trial supports the findings from the first year and shows that sheep grazing Kentucky 31 tall fescue infected with wild-type endophytes had significantly less weight gain, higher body temperatures and greater respiration rates than did the sheep on endophyte-free and AR501 infected pastures. The summer of 1997/98 was the hottest on record at the trial site. The negative weight gain of the sheep grazing wild-type tall fescue is likely to be linked to the severity and duration of heat stress during the period.

EXAMPLE 9

Effect on Insects

Argentine Stem Weevil

Tall fescue is not a favoured host of this insect and so reductions in adult feeding and larval damage due to the presence of endophytes is small. In a trial at two sites at Lincoln, New Zealand with Advance tall fescue infected with the endophytes AR501, AR502 and with endophyte-free plants, observations were carried out on the incidence of Argentine stem weevils and the damage they caused. The results are presented in Table 7.

TABLE 7

Incidence and Damage caused by Argentine Stem Weevils on Advance Tall Fescue Infected with AR501, AR502 or Endophyte-Free at Two Sites

| | Site 1 | | Site 2 | |
|---|---|---|---|---|
| Endophyte | Adult feeding score/tiller | % tillers with larval damage | Adult feeding score/tiller | % tillers with larval damage |
| AR501 | 0.30 | 4 | 0.75 | 0 |
| AR502 | 0.24 | 1 | 0.49 | 2 |
| Endophyte-free | 0.30 | 3 | 0.97 | 1 |

The only significant difference in insect damage at these two sites was that at site 2 there was less feeding on the plants infected with AR502 than on the endophyte-free plants. Observations on Argentine stem weevil feeding and tiller damage were made on an amenity tall fescue trial at Palmerston North, New Zealand in the summers of 1996/97 and 1997/98. The results are given in Table 8 below.

TABLE 8

Incidence and Damage caused by Argentine Stem Weevil to an Amenity Tall Fescue Infected with AR501, AR542 or Endophyte-Free over Two Summers

| | 1997 | | 1998 | |
|---|---|---|---|---|
| Endophyte | Adult feeding score/tiller | % tillers with larval damage | Adult feeding score/tiller | % tillers with larval damage |
| AR501 | 0.9 | 0.5 | 0.15 | 0 |
| AR542 | 1.0 | 1.0 | 0.19 | 0 |
| Endophyte-free | 1.1 | 2.5 | 0.16 | 0 |

Porina

In a choice bioassay with 3 month old larvae the endophyte in Kentucky 31 tall fescue reduced feeding by 30% when compared with the endophyte-free control.

REFERENCES

Barker, D. J.; Davies, E.; Lane, G. A.; Latch, G. C. M.; Nott, H. M. and Tapper, B. A. 1993. Effect of water deficit on alkaloid concentrations in perennial ryegrass endophyte associations. Hume, D. E.; Latch, G. C. M. and Easton, H. S. (eds). Proc. Second International Symposium on Acremonium/Grass Interactions, pp. 76–76. AgResearch, Palmerston North, New Zealand Morgan-Jones, G. and Gams, W. 1982. Notes on Hyphomycetes. XLI. An endophyte of *Festuca arundinaceae* and the anamorph of *Epichloe typhina,* a new taxa in one of two new sections of Acremonium. Mycotaxon 15: 311–318.

What is claimed is:

1. An axenic culture of an endophyte selected from the group consisting of AR501, AR502, AR510, AR542, AR572, AR577 and AR584, AGAL deposit nos. NM98/04681, NM98/04677, NM98/04678, NM98/04675, NM98/04679, NM98/04680 and NM98/04676, respectively.

2. A synthetic combination of an endophyte as claimed in claim 1 with a tall fescue cultivar.

3. A combination as claimed in claim 2 wherein said tall fescue cultivar is a temperate European type tall fescue cultivar.

4. A combination as claimed in claim 2 where said tall fescue cultivar is selected from the group consisting of Grasslands Advance, Kentucky 31, Georgia 5 and Jesup.

5. A combination as claimed in claim 2 which has been made by inoculating a said tall fescue cultivar with a said axenic culture of a said endophyte.

6. A combination as claimed in claim 2 which has been made by crossing a said synthetic endophyte/tall fescue combination with an endophyte free tall fescue cultivar to form a new tall fescue cultivar infected with said endophyte.

7. Seeds of a combination as claimed in claim 2.

8. Seeds as claimed in claim 7 which have been harvested from tall fescue plants inoculated with said endophyte.

9. Seeds as claimed in claim 7 which have been harvested from plants of said synthetic endophytes/tall fescue combination grown from seeds harvested from tall fescue plants inoculated with said endophyte or from seeds of subsequent generations of tall fescue plants so infected.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(iii) HYPOTHETICAL: NO (xi) SEQUENCE DESCRIPTION: SEQ ID NO:1:

TGGACTCGAC TTGCCCTCTC TCAG      24

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single (D) TOPOLOGY: linear (ii) MOLECULE TYPE: other nucleic acid
            (A) DESCRIPTION: /desc = "oligonucleotide"

(iii) HYPOTHETICAL: NO (xi) SEQUENCE DESCRIPTION: SEQ ID NO:2:

TGCGAGCAGC GTTTGCGTGT GCGT                                              24

(2) INFORMATION FOR SEQ ID NO:3:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (xi) SEQUENCE DESCRIPTION: SEQ ID NO:3:

GGCATGGTAT GGGCAATGAG TGTC                                              24

(2) INFORMATION FOR SEQ ID NO:4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (xi) SEQUENCE DESCRIPTION: SEQ ID NO:4:

CTGCTGCGAT GTTTTGTACT GTGG                                              24

(2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (xi) SEQUENCE DESCRIPTION: SEQ ID NO:5:

AATCGTTGTG CGAGCCATTC TGGC                                              24

(2) INFORMATION FOR SEQ ID NO:6:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO

-continued

```
    (xi) SEQUENCE DESCRIPTION: SEQ ID NO:6:

GCCCCGTCAT GCATTATCTC CTTG                                              24

(2) INFORMATION FOR SEQ ID NO:7:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (xi) SEQUENCE DESCRIPTION: SEQ ID NO:7:

CGCTCAGGGC TACATACACC ATGG                                              24

(2) INFORMATION FOR SEQ ID NO:8:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (xi) SEQUENCE DESCRIPTION: SEQ ID NO:8:

CTCATCGAGT AACGCAGGCG ACG                                               23

(2) INFORMATION FOR SEQ ID NO:9:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (xi) SEQUENCE DESCRIPTION: SEQ ID NO:9:

CATGGATGGA CAAGAGATTG CACG                                              24

(2) INFORMATION FOR SEQ ID NO:10:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (xi) SEQUENCE DESCRIPTION: SEQ ID NO:10:

TTCACTGCTA CAATTCTGTG GAGC                                              24
```